(12) United States Patent
Castellano

(10) Patent No.: US 6,474,369 B2
(45) Date of Patent: Nov. 5, 2002

(54) APPARATUS AND METHOD FOR DELIVERING A LYOPHILIZED ACTIVE WITH A NEEDLE-LESS INJECTOR

(75) Inventor: Thomas P Castellano, Santa Monica, CA (US)

(73) Assignee: Penjet Corporation, Santa Monica, CA (US)

( * ) Notice: Subject to any disclaimer, the term of this patent is extended or adjusted under 35 U.S.C. 154(b) by 0 days.

(21) Appl. No.: 10/034,561

(22) Filed: Dec. 26, 2001

(65) Prior Publication Data

US 2002/0056486 A1 May 16, 2002

Related U.S. Application Data

(60) Provisional application No. 60/286,875, filed on Apr. 27, 2001.

(51) Int. Cl.$^7$ .............................. B65B 1/04; B65B 3/04
(52) U.S. Cl. ................... 141/9; 141/2; 141/27; 141/319; 141/321; 141/383; 141/384
(58) Field of Search ......................... 141/2, 9, 18, 27, 141/100, 311 R, 312, 319–321, 329, 330, 351, 357, 363, 366, 383, 384, 391; 604/48, 56, 68, 82, 88, 412

(56) References Cited

U.S. PATENT DOCUMENTS

| | | | |
|---|---|---|---|
| 2,642,062 A | 6/1953 | May | |
| 3,507,276 A | 4/1970 | Burgess | |
| 3,688,765 A | 9/1972 | Gasaway | |
| 3,695,266 A | 10/1972 | Lussier | |
| 3,853,125 A | 12/1974 | Clark et al. | |
| 3,946,732 A | * 3/1976 | Hurscham | 604/88 |
| 4,338,980 A | 7/1982 | Schwebel et al. | |
| 4,676,781 A | 6/1987 | Phillips et al. | |
| 4,722,728 A | 2/1988 | Dixon | |
| 4,874,367 A | 10/1989 | Edwards | |
| 4,941,880 A | 7/1990 | Burns | |
| 5,009,634 A | 4/1991 | Feldman et al. | |
| 5,009,637 A | 4/1991 | Newman et al. | |
| 5,024,656 A | 6/1991 | Gasaway et al. | |
| 5,064,413 A | 11/1991 | McKinnon et al. | |
| 5,088,996 A | * 2/1992 | Kopfer et al. | 141/329 |
| 5,593,388 A | 1/1997 | Phillips | |
| 5,730,723 A | 3/1998 | Castellano et al. | |
| 5,746,714 A | * 5/1998 | Salo et al. | 604/143 |
| 5,840,381 A | 11/1998 | Ohtsuka | |
| 5,851,198 A | 12/1998 | Castellano et al. | |
| 5,891,085 A | 4/1999 | Lilley et al. | |
| 6,168,587 B1 | 1/2001 | Bellhouse et al. | |
| 6,223,786 B1 | * 5/2001 | Castellano | 141/100 |
| 6,302,160 B2 | 10/2001 | Castellano | |
| 6,309,371 B1 | 10/2001 | Deboer et al. | |
| 6,406,455 B1 | 6/2002 | Willis et al. | |

FOREIGN PATENT DOCUMENTS

| | | |
|---|---|---|
| CA | 1258019 | 8/1989 |
| EP | 0295917 | 12/1988 |
| FR | 2749169 | 12/1997 |
| WO | WO 8908469 | 9/1989 |
| WO | WO 9503844 | 2/1995 |
| WO | WO 96 28202 | 9/1996 |
| WO | 9725015 | 7/1997 |

* cited by examiner

Primary Examiner—Timothy L. Maust
(74) Attorney, Agent, or Firm—Pillsbury Winthrop LLP

(57) ABSTRACT

A device for storing and mixing an injectate includes a fluid holder removably coupled to an ampoule. The fluid holder initially contains a fluid and the ampoule initially contains a dry reagent. A breakable membrane may be included between the fluid holder and ampoule to prevent the undesirable mixing of the fluid with the dry reagent. Upon application of force to a plunger rod disposed within the fluid holder, fluid is introduced into the ampoule wherein it is mixed with the dry reagent to create an injectable mixture. Air or gas present in the ampoule may be removed therefrom; the fluid holder may be decoupled from the ampoule; and the ampoule may be further coupled to a needle-less injector for administration of an injection of the mixture. The device is particularly useful for lyophilized pharmaceuticals that rapidly lose medicinal efficacy once in solution form.

33 Claims, 13 Drawing Sheets

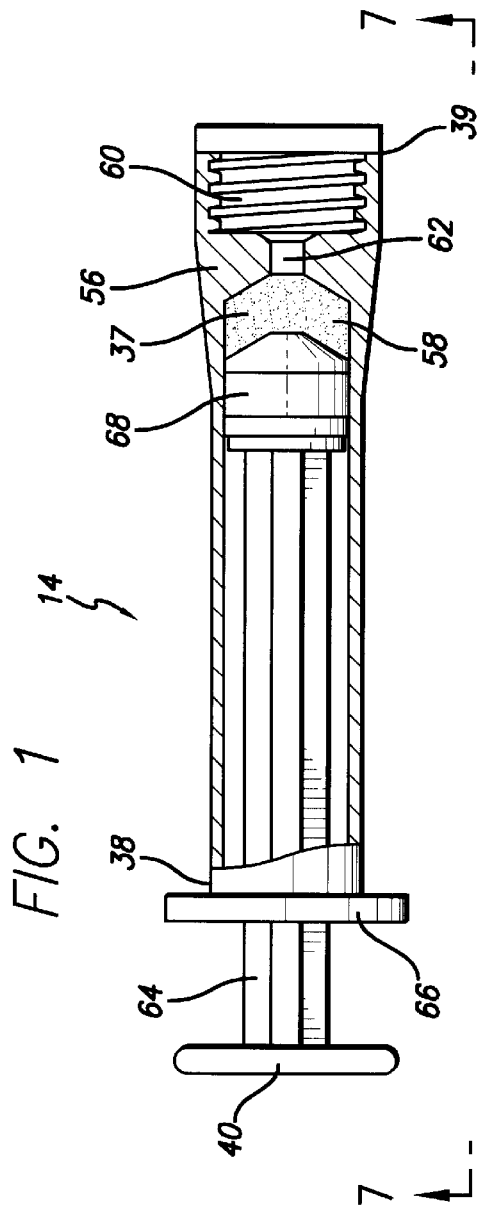
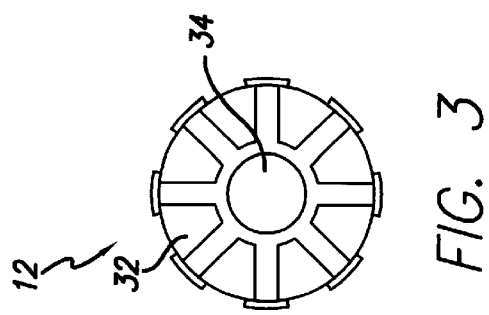
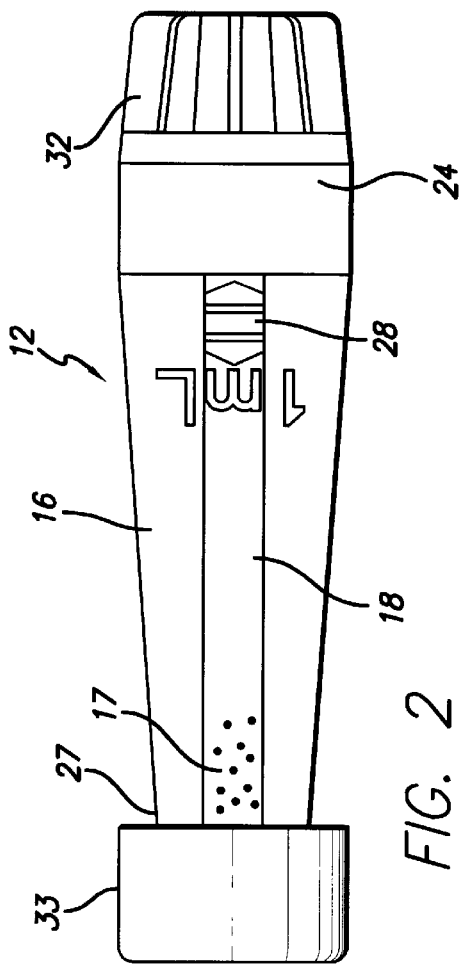

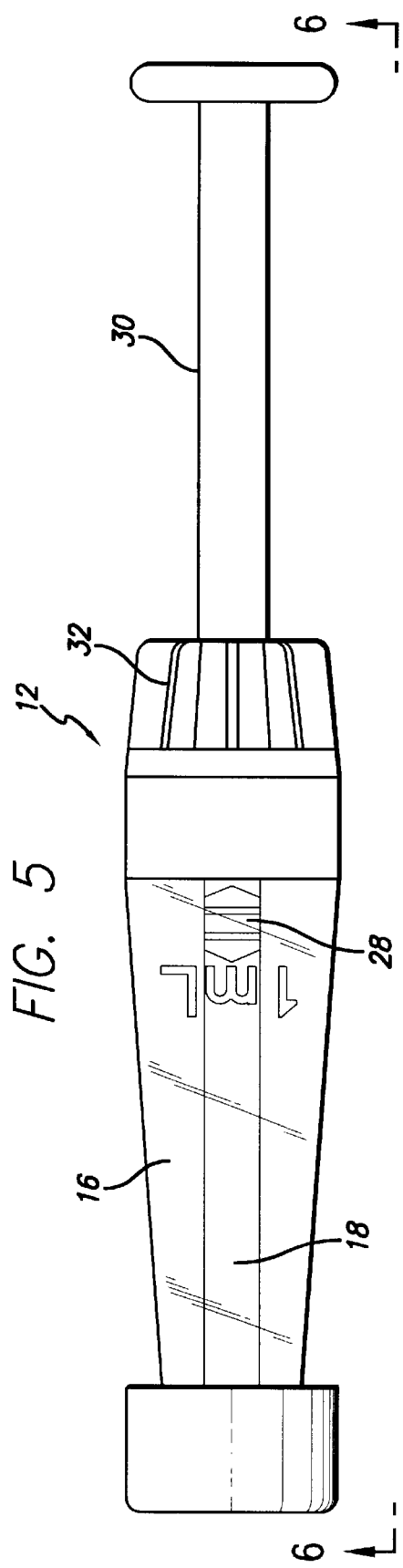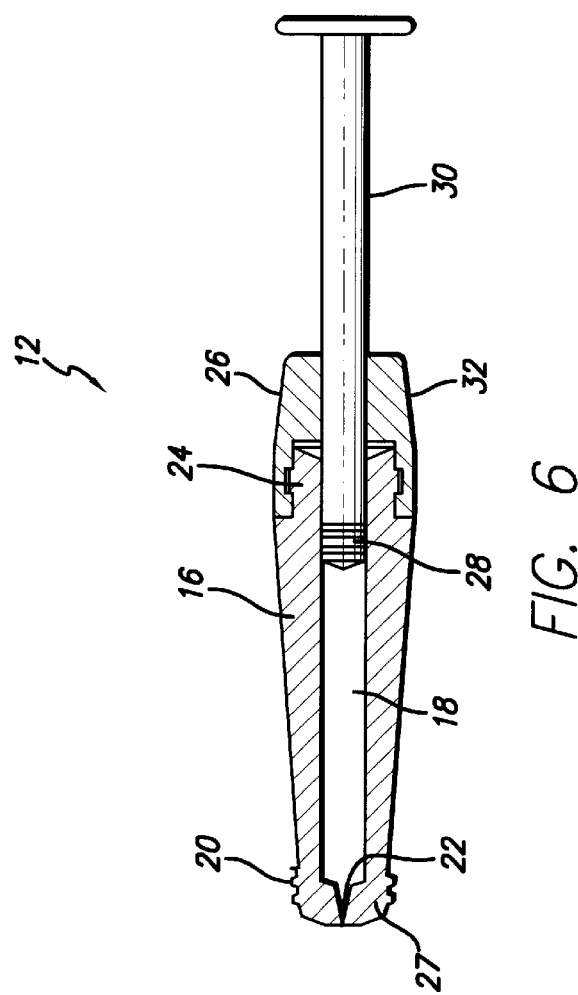
FIG. 5
FIG. 6

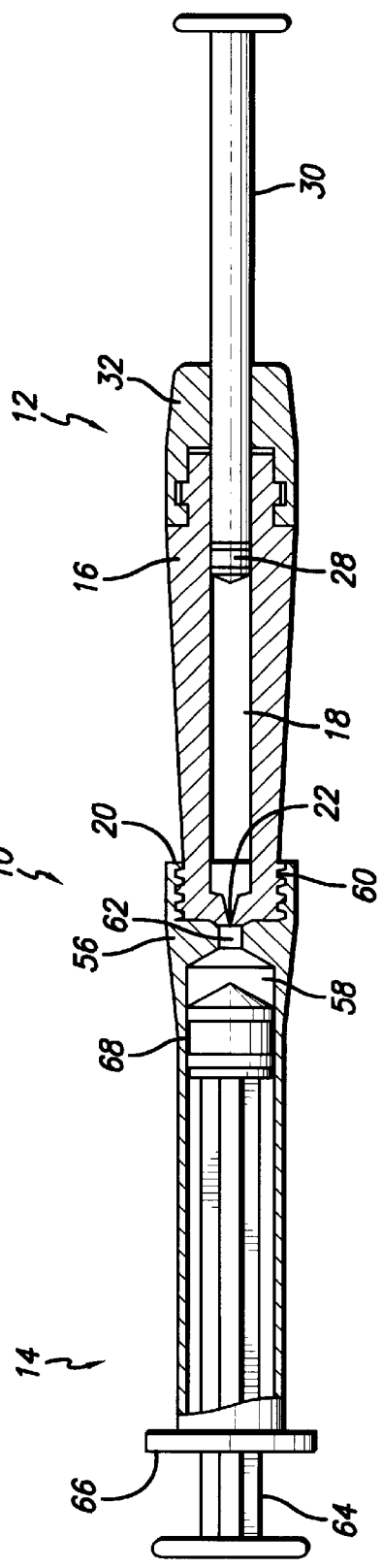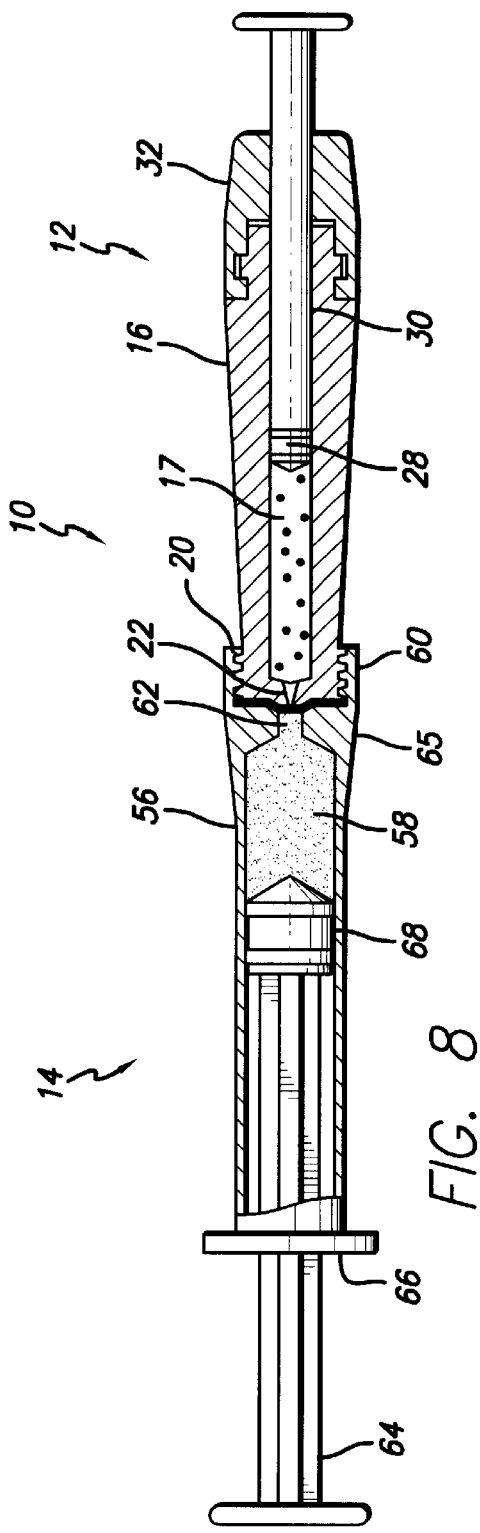

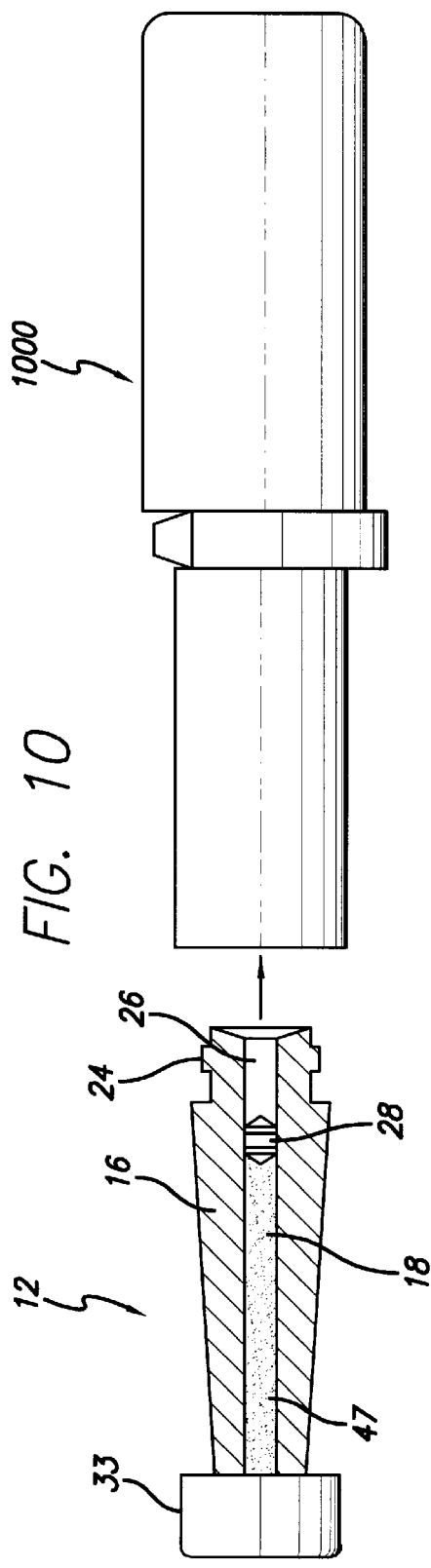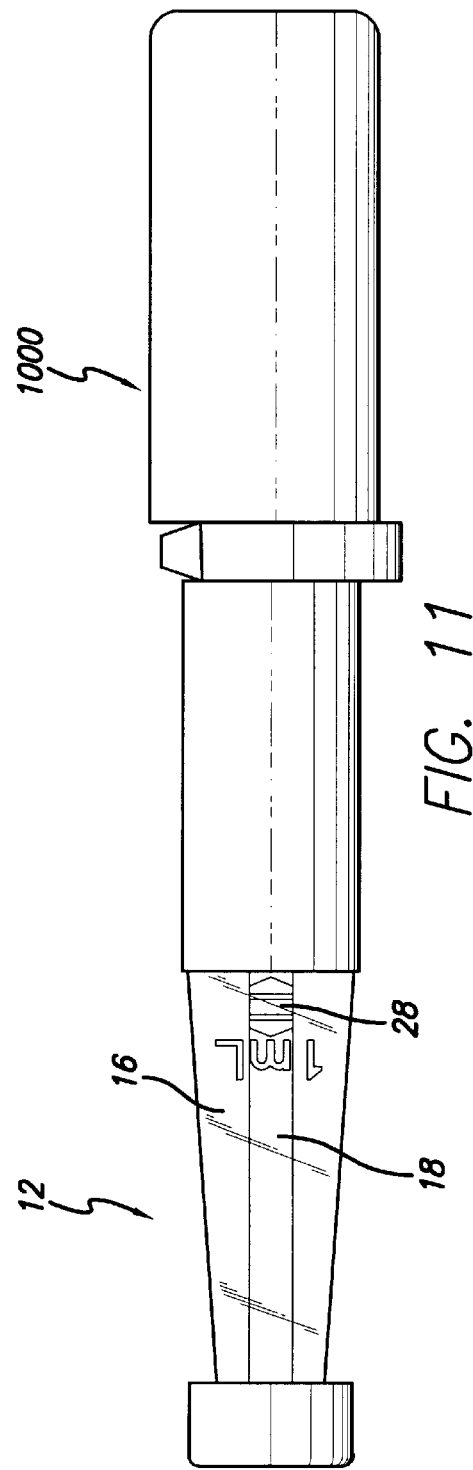

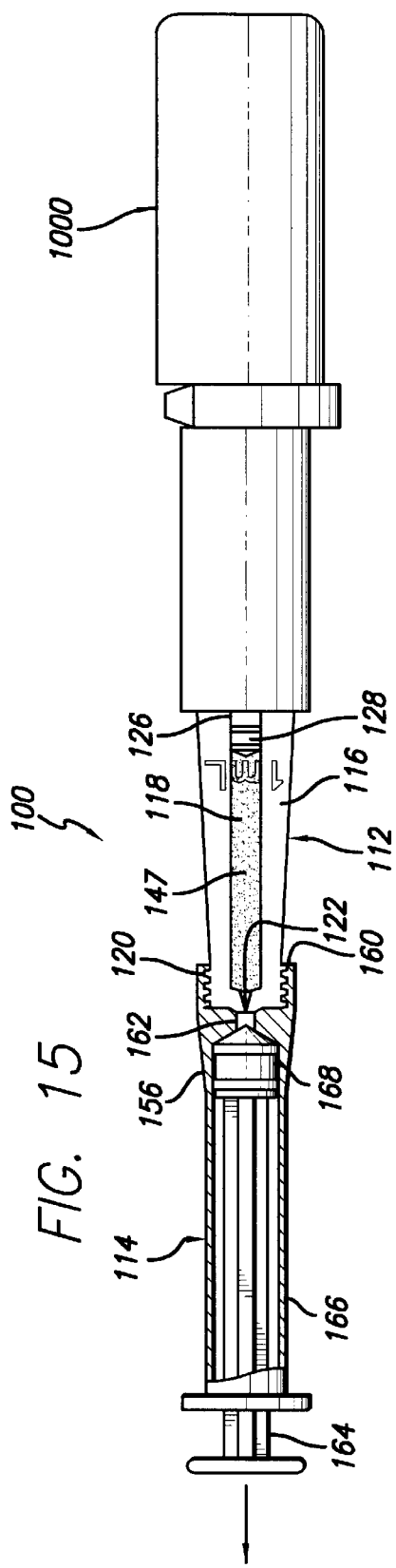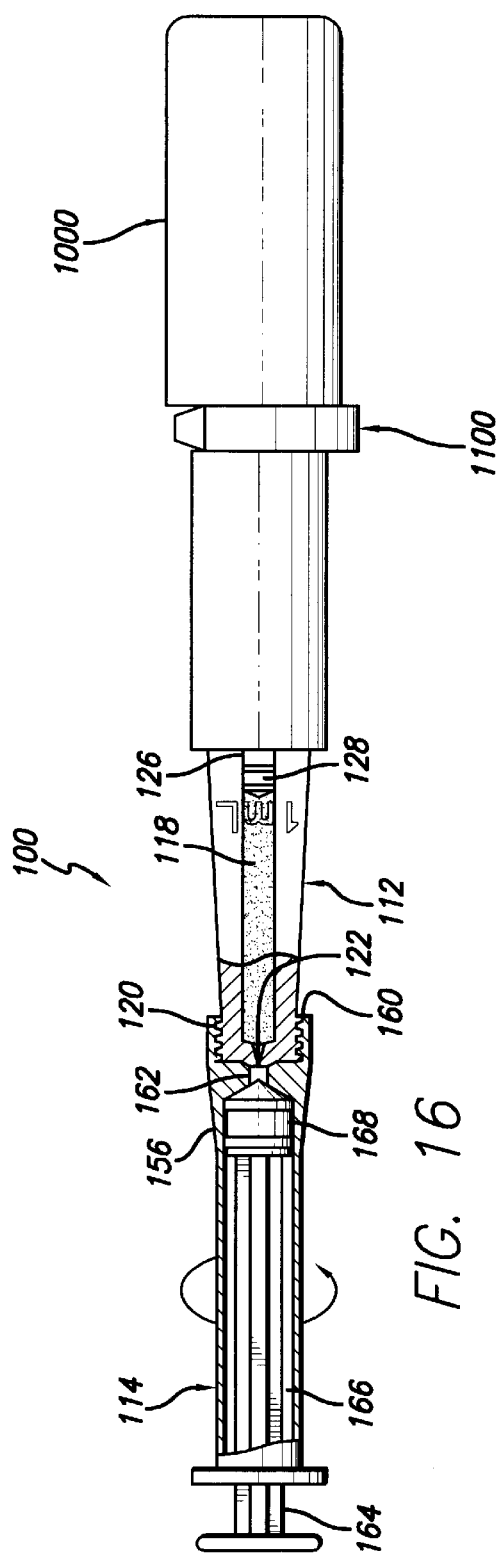

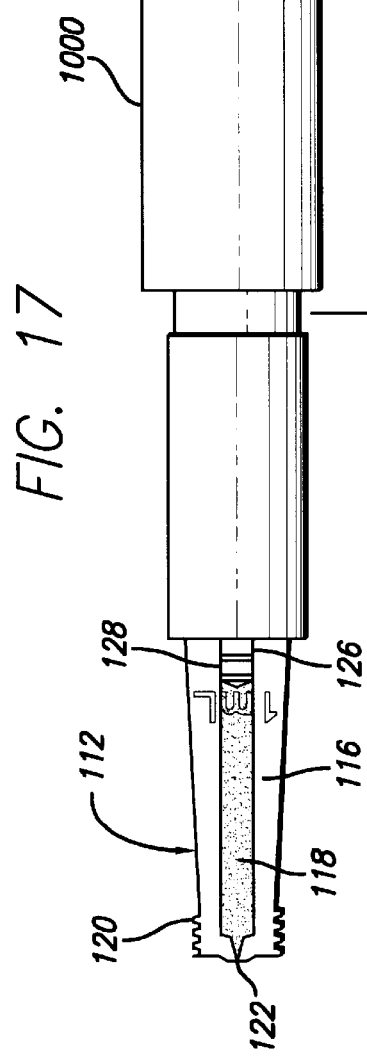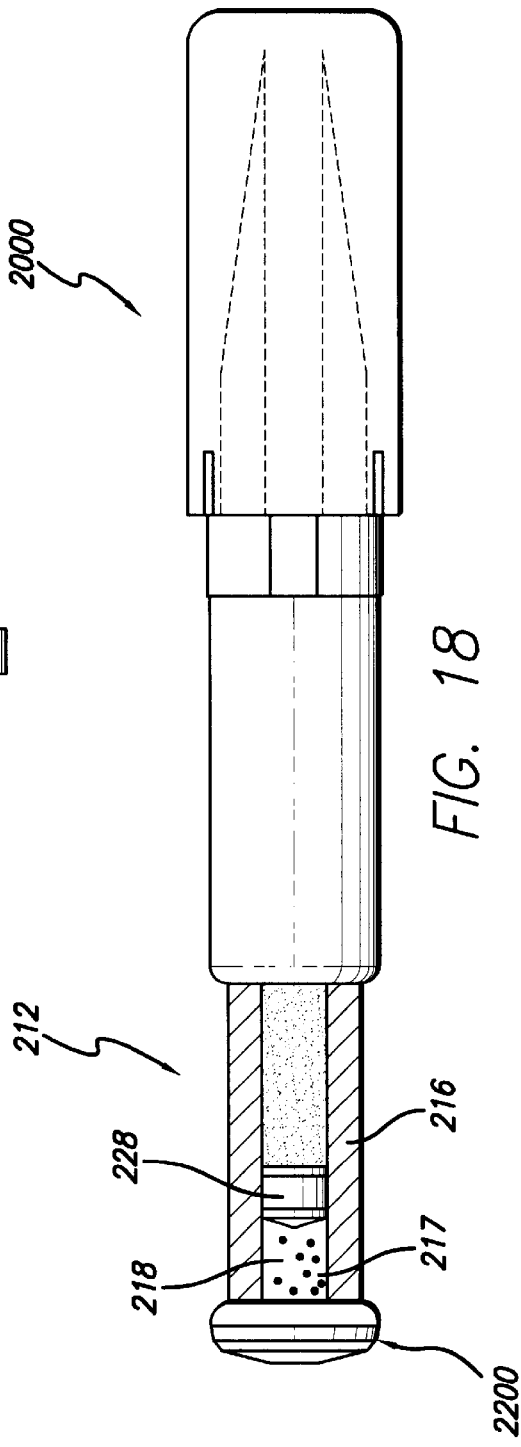
FIG. 17
FIG. 18

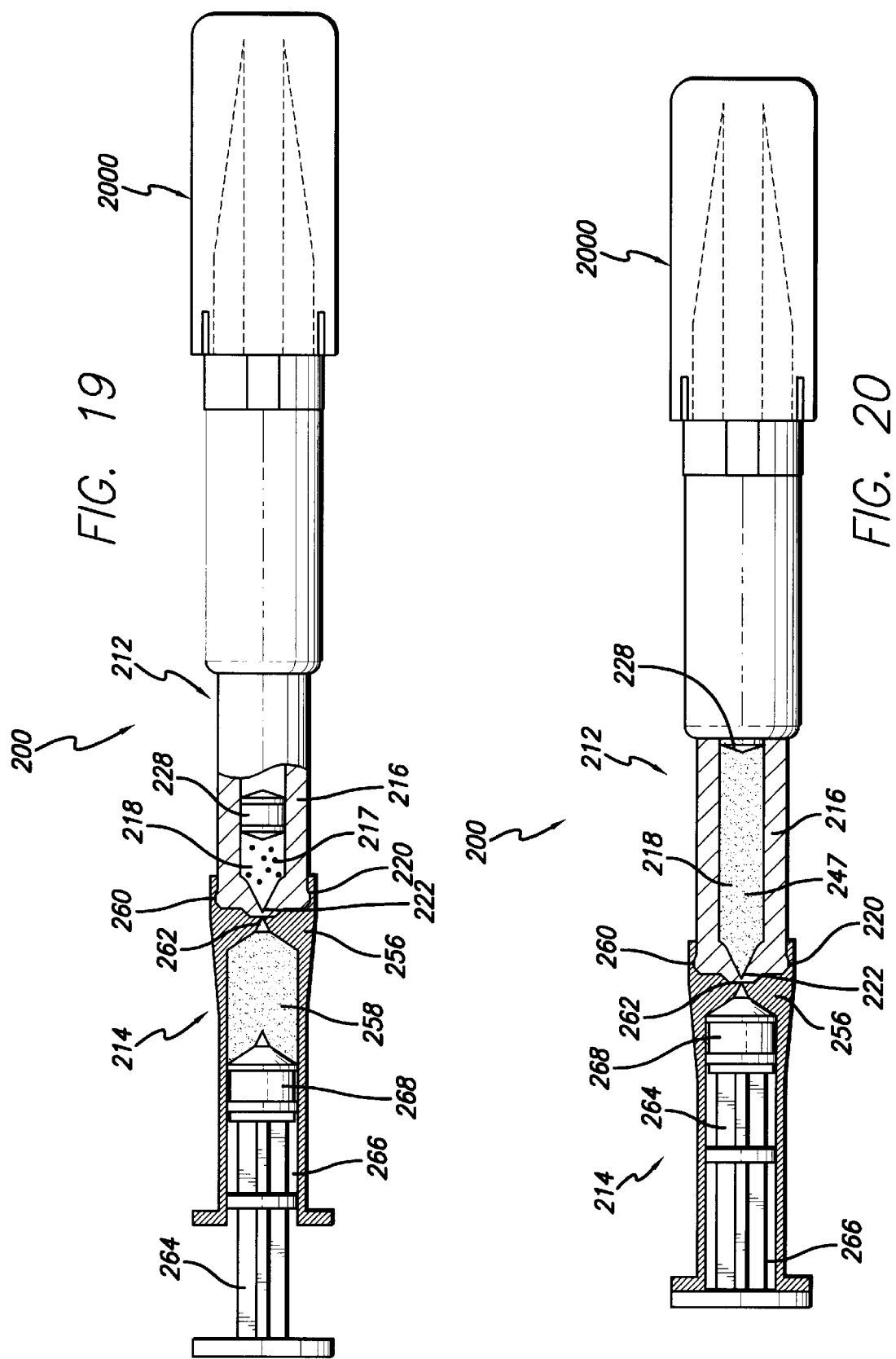

APPARATUS AND METHOD FOR DELIVERING A LYOPHILIZED ACTIVE WITH A NEEDLE-LESS INJECTOR

RELATED APPLICATIONS

This application is related to U.S. patent application Ser. No. 09/433,916, filed Nov. 3, 1999, now U.S. Pat. No. 6,302,160, which is a continuation-in-part of U.S. patent application Ser. No. 09/192,145, filed Nov. 14, 1998, now U.S. Pat. No. 6,223,786. This application generally relates to U.S. patent application Ser. No. 09/834,476, filed Apr. 13, 2001 and U.S. patent application Ser. No. 10/086,374, filed Oct. 22, 2001. Further, this application generally relates to U.S. patent application Ser. No. 10/011,534, filed Oct. 26, 2001, which is a divisional application of U.S. patent application Ser. No. 09/566,928, filed May 6, 2000; to provisional U.S. patent application Ser. No. 60/286,875, filed Apr. 27, 2001; and to U.S. patent application Ser. No. 09/215,769, filed Dec. 19, 1998, now U.S. Pat. No. 6,063,053, which is a continuation of U.S. patent application Ser. No. 08/727,911, filed Oct. 9, 1996, now U.S. Patent No. 5,851,198, which is a continuation-in-part of U.S. patent application Ser. No. 08/719,459, filed Sep. 25, 1996, now U.S. Pat. No. 5,730,723, which is a continuation-in-part of U.S. patent application Ser. No. 08/541,470, filed Oct. 10, 1995, now abandoned. This application is further generally related to U.S. patent application Ser. No. 09/192,079, filed Nov. 14, 1998, now U.S. Pat. No. 6,080,130, and to U.S. patent application Ser. No. 09/808,511, filed Mar. 14, 2001.

FIELD OF THE INVENTION

This invention relates to devices and methods for storing and mixing injectants, and to devices and methods for filling an ampoule of a needle-less injector prior to an injection. In particular embodiments, the invention relates to devices and methods for filling an ampoule of a needle-less injector with a medication that must be mixed just prior to administration of an injection, and to the storage of such medication prior to mixing and filling. More particularly, the invention relates to injectable medications wherein one component of the medication is a reagent that is stored in dry form.

BACKGROUND OF THE INVENTION

A number of medications are maximally effective when mixed immediately prior to administration to a patient. These medications may include multiple liquids, or, alternatively, at least one liquid that is mixed with an active stored in solid form. Generally, the need for mixing immediately prior to injection is due to the rapid loss of medicinal efficacy of a particular reagent included in the medication once the components thereof are combined.

This is often the case with lyophilized actives. Lyophilized actives are essentially freeze-dried pharmaceuticals that do not maintain efficacy when stored for a substantial period of time in solution. In fact, most lyophilized actives become medicinally ineffective once in solution for more than a few hours, and many such actives lose effectiveness after just a few minutes. This rapid loss of medicinal efficacy creates a storage and delivery problem, frequently obviated by storing the lyophilized active in solid form and mixing it with a liquid immediately prior to injection.

The liquid with which a lyophilized active is mixed often adds little therapeutic quality to the final mixture. Rather, the liquid is usually a delivery vehicle, able to carry the otherwise dry active through a needle into the tissue of a patient. Since liquid delivery vehicles present the same efficacy loss problems discussed above, delivery of lyophilized actives by other means has been attempted. For instance, in one system lyophilized actives are coated on the surface of gold particles, and helium gas is used to accelerate these coated particles against and into the skin surface of a patient. This method has several drawbacks, however, as it can be painful to a recipient, and because the lyophilized active may not be delivered to an appropriate segment of a patient's tissue. Frequently such actives require subdermal delivery, which is not readily achieved by the acceleration method.

In general, a typical injection is performed with a syringe that pierces the skin with a needle to deliver medication to a desired location on a body. Oftentimes, the syringes are pre-filled with a medication. However, if a particular medication does not have a long shelf life, as is generally the case with lyophilized actives in solution, the medication must be mixed just prior to an injection to maintain potency. This requires the medication to be mixed externally to the syringe and then drawn in using needles or the like. After drawing in the medication, the injection may be administered in a normal manner. But, after the injection there are one or more needles that need to be disposed of, increasing both cost and the potential for health hazards from exposure to used needles.

As an alternative to needle delivery injections, needle-less medication injections have been performed with "permanent gun" instruments, generally referred to as "jet injectors." These devices use either a compression spring or a compressed inert gas to propel a fluid medication (via a push rod plunger) through a small orifice (an injector nozzle) which rests perpendicular to and against the injection site. The fluid medication is generally accelerated at a high rate to a speed of between about 800 feet per second (fps) and 1,200 fps (approximately 244 and 366 meters per second, respectively). This causes the fluid to pierce through the skin surface without the use of a needle, resulting in the medication being deposited in a flower pattern under the skin surface.

Reusable jet injectors can accept pre-loaded medication cartridges, but the cartridges must be pre-loaded just prior to an injection for certain medications with short shelf lives. The procedure is to again use a needle and a syringe to mix and then load the medication in the cartridge prior to an injection. After drawing in the medication, the needle-less injection is administered in a normal manner. But, after the injection there are again one or more needles that need to be disposed of, presenting problems of cost and safety, as described above.

Single use needle-less jet injectors offer an alternative to multi-use, needle-less injectors, since they are low cost and can be pre-loaded at the point of manufacture. However, if the medication does not have a long shelf life, the pre-loading is impractical for the same reasons discussed above. Thus, single-use, needle-less injectors have generally not been usable with medications that must be mixed prior to injection. An alternative to overcome this drawback was to include a two compartment ampoule in the injector, which is opened up with a piercing mechanism such that two components are combined together to mix a medication as an injection takes place. Although this obviates the need for needles, the results are unsatisfactory, since the medication is not always thoroughly mixed and properly deposited under the skin. In addition, improper mixing can allow the medication (large molecule medications in particular) to be destroyed or altered during the injection process. Further, the piercing mechanism included in the ampoule may block or obscure the orifice, or jam the needle-less injector leading to an improper injection.

U.S. Pat. No. 6,223,786 and U.S. Pat. No. 6,302,160 describe devices and methods for mixing medications and filling the ampoule of a needle-less injector, thus obviating some of the limitations inherent in using needle-less injectors for the administration of actives with short shelf lives.

SUMMARY OF THE DISCLOSURE

It is an object of an embodiment of the present invention to provide an improved device and method for filling an ampoule of a needle-less injector with a mixture that is prepared just prior to administration of an injection, and to the storage of the components of such mixture prior to mixing and filling, that obviates for practical purposes, the above-mentioned limitations.

According to an embodiment of the present invention, an apparatus for preparing a mixture and filling an ampoule of a needle-less injector suitable for injecting the mixture includes an ampoule and a fluid holder. The ampoule may initially contain a dry reagent, and the fluid holder may initially contain a fluid. Preferably, the fluid holder also includes a fluid plunger rod, and the ampoule is coupled to the fluid holder to provide fluid communication therebetween. The fluid plunger rod may be depressed, loading the fluid into the ampoule where it mixes with the dry reagent, thus creating a mixture in the ampoule. In most preferred embodiments, the fluid holder includes a breakable membrane that prevents the fluid from being in communication with the dry reagent until the breakable membrane is broken by the application of pressure upon the fluid plunger rod. In yet further embodiments, the ampoule may include an ampoule plunger rod. After the mixture is prepared, the ampoule plunger rod may be depressed to expel air or gas either into the fluid holder from the ampoule of the needle-less injector, or to the local atmosphere if the fluid holder has already been detached from the ampoule. If the fluid holder has not been detached from the ampoule, the fluid holder plunger rod may be partially withdrawn to pull air or gas from the ampoule into the fluid holder. Most preferably, the mixture of the fluid and the dry reagent is prepared just prior to injection of the mixture due to a short shelf life of the mixture. After mixing and filling is completed, the fluid holder may be detached from the ampoule, the ampoule may be further attached to a needle-less injector and an injection may be administered. In alternate embodiments, the entire housing of a needle-less injector may be the ampoule to which the fluid holder is coupled.

According to another embodiment of the present invention, a method of preparing a mixture and filling an ampoule of a needle-less injector suitable for injecting the mixture includes the steps of: providing an ampoule containing a dry reagent; providing a fluid holder containing a fluid; providing the fluid holder with a fluid plunger rod; coupling the ampoule to the fluid holder to provide fluid communication therebetween; and depressing the fluid plunger rod to load the fluid into the ampoule to mix the fluid and the dry reagent. Further embodiments may include the additional steps of: providing the fluid holder with a breakable membrane; and depressing the fluid plunger rod to rupture the breakable membrane, such that the fluid can be in communication with the dry reagent. Still further embodiments may include the additional steps of providing the ampoule with an ampoule plunger rod; and depressing the ampoule plunger rod after the ampoule is loaded with fluid and the fluid and dry reagent are mixed, to expel air or gas into the fluid holder from the ampoule of the needle-less injector or to the local atmosphere in those instances where the fluid holder and the ampoule have already been detached from one another. If the fluid holder has not been detached from the ampoule, then an embodiment may include the step of: at least partially withdrawing the fluid holder plunger rod to pull air or gas from the ampoule into the fluid holder. Preferably, the step of filling the ampoule thereby creating the mixture of the fluid and the dry reagent occurs just prior to injection of the mixture due to a short shelf life of the mixture. The method may include the step of attaching the ampoule to a needle-less injector after filling the ampoule with the fluid and creating the mixture of the fluid and the dry reagent.

Other features and advantages of the invention will become apparent from the following detailed description, taken in conjunction with the accompanying drawings, which illustrate, by way of example, various features of embodiments of the invention.

BRIEF DESCRIPTION OF THE DRAWINGS

FIG. 1 is a side plan view of a fluid holder in accordance with an embodiment of the present invention;

FIG. 2 is a side plan view of an ampoule for a needle-less injector in accordance with an embodiment of the present invention;

FIG. 3 is an end plan view of the ampoule shown in FIG. 2 in accordance with an embodiment of the present invention;

FIG. 5 is a side plan view of the ampoule of FIGS. 2 and 3 combined with the plunger rod shown in FIG. 4 in accordance with an embodiment of the present invention;

FIG. 6 is a cross-sectional view of the ampoule and plunger rod as shown along the line 6—6 in FIG. 5 in accordance with an embodiment of the present invention;

FIG. 7 is a cross-sectional view of the fluid holder, as shown along line 7—7 in FIG. 1 coupled to the ampoule and plunger rod as shown in FIG. 6 in accordance with an embodiment of the present invention;

FIG. 8 is a cross-sectional view of the fluid holder and ampoule as shown in FIG. 7, including a fluid, a dry reagent and a breakable membrane in accordance with an embodiment of the present invention;

FIG. 10 is a partial cross-sectional view and side plan view of an ampoule filled with a mixture that is to be mated to a needle-less injector in accordance with an embodiment of the present invention;

FIG. 11 is a side plan view of an assembled needle-less injector prior to administering an injection in accordance with an embodiment of the present invention;

FIG. 15 is a cross-sectional view of the fluid holder, ampoule and needle-less injector depicted in FIG. 13 after the mixture has been created, indicating the fluid holder plunger rod being withdrawn to remove air or gas from the ampoule in accordance with an embodiment of the present invention;

FIG. 16 is a cross-sectional view of the fluid holder, ampoule and needle-less injector depicted in FIG. 13 prior to removal of the fluid holder to permit an the administration of an injection in accordance with an embodiment of the present invention;

FIG. 17 is a partial cross-sectional and side plan view of an assembled needle-less injector prior to administering an injection in accordance with another embodiment of the present invention;

FIG. 18 is a side plan view of a needle-less injector with a cap, the needle-less injector including a housing in accordance with an embodiment of the present invention;

FIG. 19 is a side plan view of the needle-less injector depicted in FIG. 18 coupled to a fluid holder illustrated in cross-section, prior to mixing the fluid contained in the fluid holder with the dry reagent contained in the needle-less injector housing in accordance with an embodiment of the present invention;

FIG. 20 is a cross-sectional view of the fluid holder and the needle-less injector housing shown in FIG. 19, after the fluid is transferred from the fluid holder to the needle-less injector housing and the mixture of the fluid and the dry reagent is created in accordance with an embodiment of the present invention;

DETAILED DESCRIPTION OF THE PREFERRED EMBODIMENTS

Figure 4A:
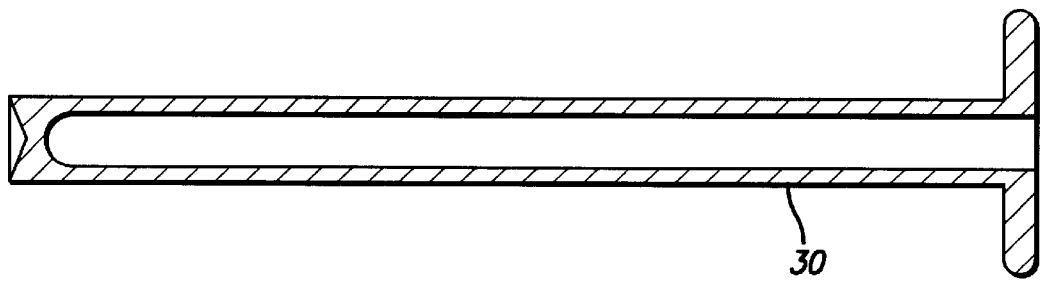
FIG. 4A is a cross-sectional view of an ampoule plunger rod in accordance with an embodiment of the present invention.
Figure 4B:
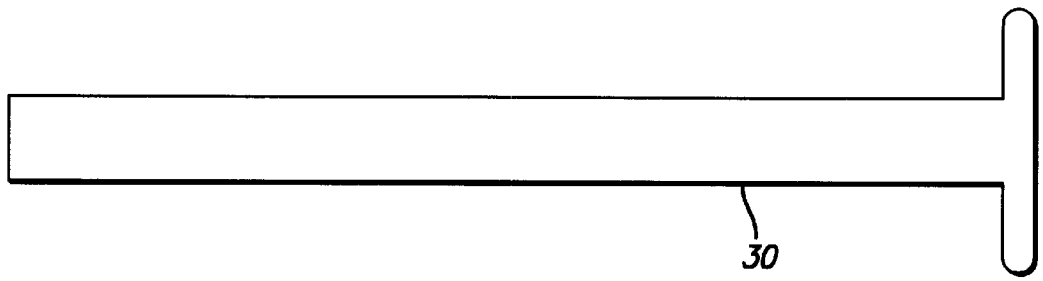
FIG. 4B is a side plan view of the ampoule plunger rod in accordance with an embodiment of the present invention.

As shown in the drawings for purposes of illustration, the invention is embodied in a device and method for mixing a fluid with a dry reagent to create a mixture, and for filling an ampoule of a needle-less injector with the mixture prior to administration of an injection. Preferably, the device and method is for use with human beings or other animals. However, it will be recognized that further embodiments of the invention may be used in other applications requiring needle-less injection, such as passing injectable materials through a porous membrane or the like.

The dry reagent used in accordance with the present invention may include, but is not limited to, lyophilized reagents, agents, actives, pharmaceuticals, drugs or the like injectants stored in solid, powder, particulate, dust, ash or other substantially dry or solid-state form; and non-reagents that possess some therapeutic or medicinal quality. Other substances may be included as dry reagents in accordance with embodiments of the instant invention, as well, though they possess no substantial medicinal or therapeutic qualities, yet are suitable for needle-less injection.

The fluid used in accordance with the present invention may include, but is not limited to, sterile water, saline, buffered solutions or other solvents or diluents that may be mixed with a dry reagent to form a mixture suitable for needle-less injection.

The needle-less injectors suitable for use in accordance with the system and method of the instant invention may operably receive an ampoule that contains a mixture for injection. However, various needle-less injectors also suitable for use in accordance with the system and method of the instant invention may include a needle-less injector housing that acts as an ampoule; this housing not being readily separable from the remainder of the needle-less injector. Thus, the term ampoule as used herein includes both conventional ampoules as well as the housings of needle-less injectors that do not require such conventional ampoules.

As depicted in FIG. 1, a fluid holder 14 may include a generally cylindrical body 56, with attachment means 60 on a mating end 39. The attachment means 60 may be configured as a screw threading (as depicted in FIG. 1) or a snap fitting 260 (as depicted in FIG. 20), though other suitable mechanisms for removably coupling the fluid holder 14 to an ampoule may be utilized, such as friction fittings or the like. The fluid holder 14 may further include an interior cavity 37 that is open to the exterior at the plunger rod end 38 of the body 56, and which terminates at an orifice 62 near the mating end 39.

The fluid holder 14 may further include a fluid holder plunger rod 64 that is slidably disposed within the interior cavity 37 of the body 56. The fluid holder plunger rod 64 may protrude from within the body 56 at the plunger rod end 38. A grip 66 may further be included upon the exterior of the body 56 at or near the plunger rod end 38, to provide a user with a means of supporting his fingers while dispensing the contents of the fluid holder 14. A thumb rest 40 may also be included on the fluid holder plunger rod 64 to similarly provide a user with a means of supporting his thumb while dispensing the contents of the fluid holder 14. The fluid holder 14 may be alternately operated with a variety of finger configurations.

The fluid holder 14 may further include a fluid plunger 68 disposed within the interior cavity 37, which is in mechanical contact with the fluid holder plunger rod 64 at one end and with the fluid 58 contained within the interior cavity 37 at its other end. Most preferably, the application of force to the thumb rest 40 of the fluid holder plunger rod 64 causes the fluid holder plunger rod 64 to move axially toward the mating end 39 of the fluid holder 14. The movement of the fluid holder plunger rod 64 through the interior cavity 37 may push the fluid plunger 68 in a similar axial direction, forcing the fluid 58 through the orifice 62 of the body 56. Similarly, the reverse movement of the fluid holder plunger rod 64 may cause the fluid plunger 68 to move in an axial direction away from the orifice 62. When the fluid 58 has already been dispensed into an ampoule to which the fluid holder 14 is coupled, then the reverse movement of the fluid holder plunger rod 64 may be desirable to remove air or gas contained in the ampoule.

In preferred embodiments, the force needed to slidably depress the fluid holder plunger rod 64 does not require the use of any rotational motion on the part of the user. Rather, the fluid holder plunger rod 64 is most preferably configured to be slidably depressed in a rotation-free manner.

As depicted in FIG. 2, an ampoule 12 may include a generally cylindrical body 16, with ampoule attachment means 20 on a dispensing end 27 (as depicted in FIG. 6). The ampoule attachment means 20 may be configured as a screw threading (as depicted in FIG. 6) or a snap fitting 220 (as depicted in FIG. 20), though other suitable mechanisms for removably coupling the ampoule 12 to fluid holder 14 may be utilized, such as friction fittings or the like. The dispensing end may further include an orifice 22, which provides communication between an interior cavity 18 of the ampoule 12 and the exterior of the ampoule 12. In alternate embodiments, there may be multiple orifices (not shown) disposed upon the ampoule. The inclusion of multiple orifices may be advantageous for particular injectants, and are contemplated as being within the scope of the present invention.

The interior cavity 18 of the ampoule 12 may include a plunger 28 slidably disposed therein. The ampoule 12 may further include a cap 33 on the dispensing end 27, and a bushing 32 on the needle-less injector end 24. The bushing 32 may further include a bushing hole 34 (as depicted in FIG. 3) to allow an ampoule plunger rod 30 to slidably reside within the bushing 32 (as depicted in FIG. 5). The bushing 32 may be removed from the ampoule 12 to couple the ampoule 12 to a needle-less injector 1000 (as depicted in FIG. 10). A dry reagent 17 may be included in the interior cavity 18 between the plunger 28 and the dispensing end 27 of the ampoule 12.

Figure 9:
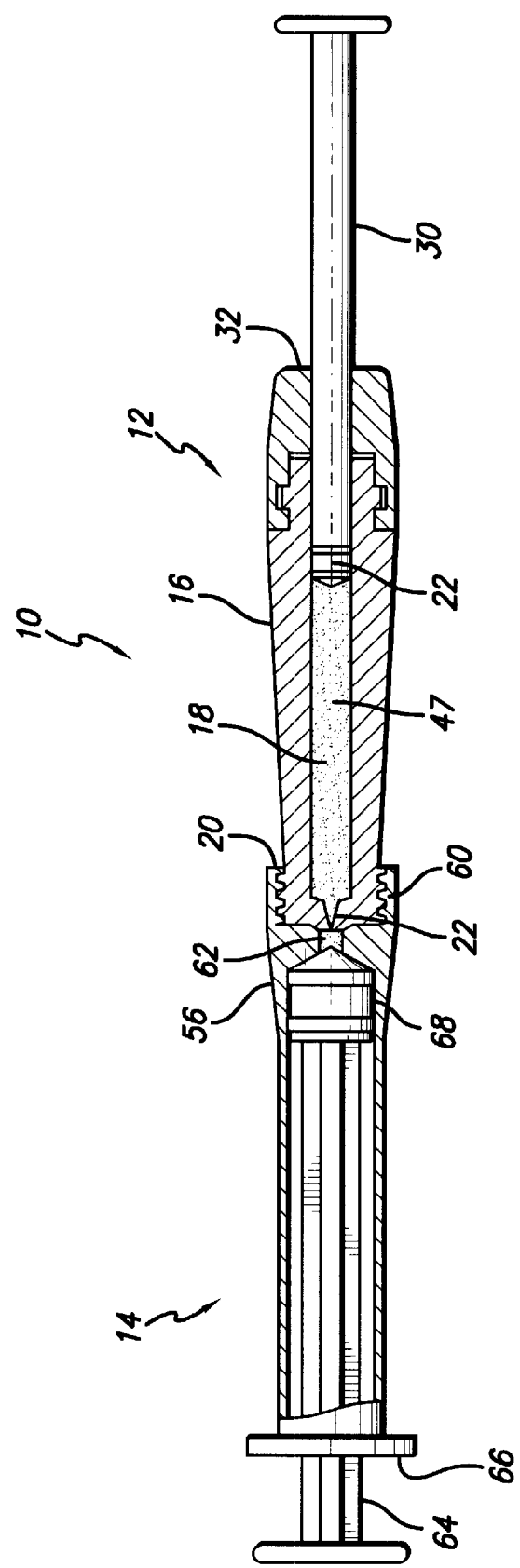
FIG. 9 is a cross-sectional view of the fluid holder and ampoule shown in FIG. 7, after the fluid has been loaded from the fluid holder into the ampoule wherein it has been mixed with the dry reagent included in the ampoule, thereby creating the mixture in the ampoule in accordance with an embodiment of the present invention.

As further illustrated in FIG. 6, the ampoule plunger rod 30 may protrude from within the interior cavity 18 at the needle-less injector end 24 of the ampoule 12, and may further be in mechanical contact with the plunger 28. In operation, after a mixture 47 of the dry reagent 17 and fluid 58 is created between the plunger 28 and the dispensing end 27 of the ampoule 12 in the interior cavity 18 (as depicted in FIG. 9), force may thereafter be applied to the ampoule plunger rod 30 to move the plunger 28 in the axial direction of the dispensing end 27 of the ampoule 12, thereby expelling undesirable air or gas from the interior cavity 18 through the orifice 22. If the fluid holder 14 remains coupled to the ampoule 12 after the mixture is created, then the air or gas may be expelled into the fluid holder 14. However, if the fluid holder 14 has been decoupled from the ampoule 12, then the air or gas may be expelled to the local atmosphere by applying force to the ampoule plunger rod 30.

FIGS. 7–11 illustrate the operation of an embodiment of the instant invention. FIG. 7 depicts the combination of the ampoule 12 with the fluid holder 14, though no fluid or dry reagent is illustrated therein. FIG. 8 depicts the same combination with a fluid 58 contained within the fluid holder 14 and with a dry reagent 17 contained within the ampoule 12. FIG. 8 further depicts a breakable membrane 165 configured between the fluid holder 14 and the ampoule 12. As discussed in greater detail below, the breakable membrane 165 may prevent the mixing of the dry reagent 17 and the fluid 58 until sufficient force is applied to the fluid holder plunger rod 64 such that the breakable membrane 165 ruptures. FIG. 9 depicts the same combination, without the membrane, the fluid holder plunger rod 64 having been depressed to load the fluid 58 into the interior cavity 18 of the ampoule 12, wherein it has mixed with the dry reagent to form a mixture 47. The introduction of fluid 58 may result in the axial movement of the plunger 28 and ampoule plunger rod 30 away from the orifice 22. FIG. 10 depicts the ampoule 12 being attached to the needle-less injector 1000 once it has been filled with the mixture 47, decoupled from the fluid holder 14 and breakable membrane 165, and the bushing 32 and ampoule plunger rod 30 have been removed. The cap may be temporarily placed back on the ampoule 12 after the mixture is created, but due to the fact that administration of a needle-less injection generally follows soon after mixing, this replacement of the cap is not required. Finally, FIG. 11 depicts the needle-less injector 1000 and ampoule 12 assembled prior to an injection.

Figure 12:
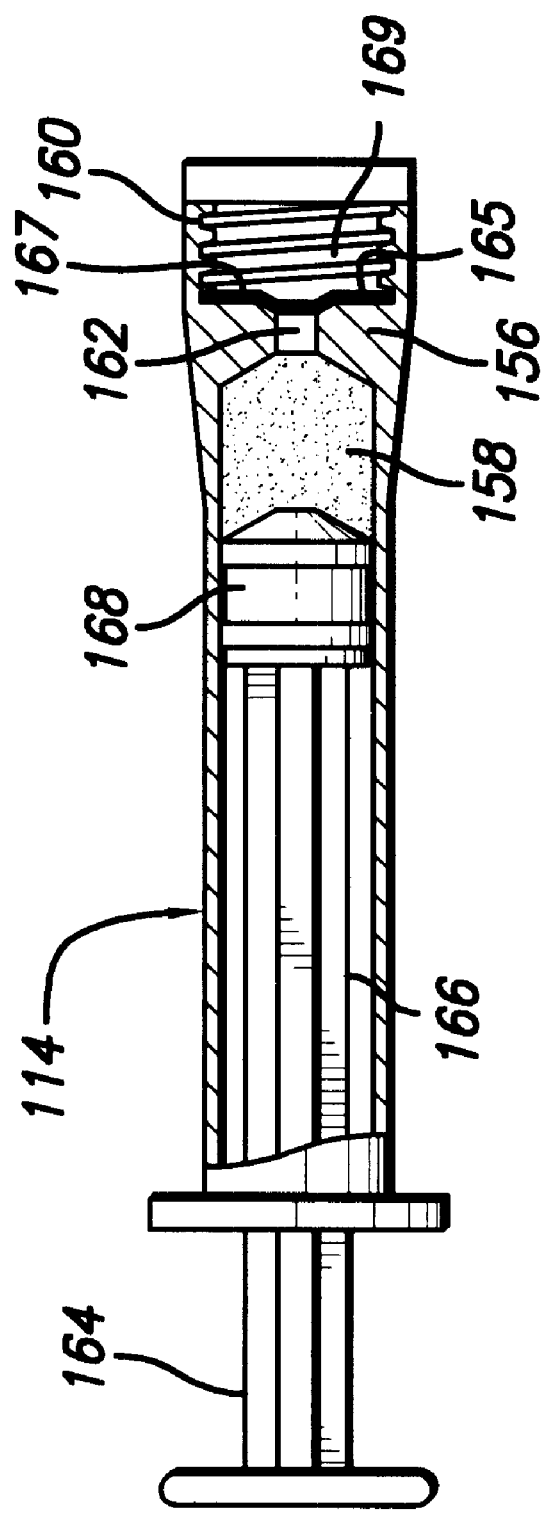
FIG. 12 is a cross-sectional view of a fluid holder including a breakable membrane in accordance with an embodiment of the present invention.
Figure 13:
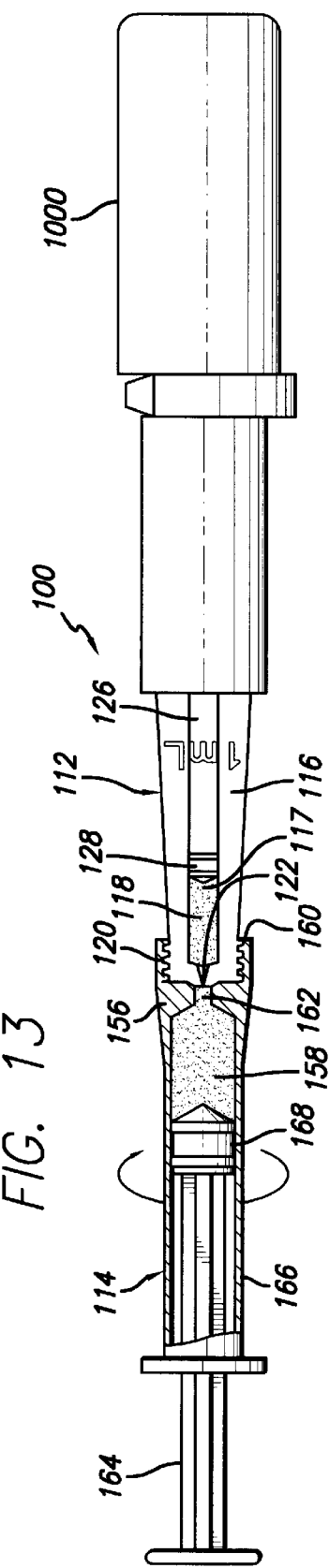
FIG. 13 is a cross-sectional view of a fluid holder coupled to an ampoule that is further coupled to a needle-less injector, prior to mixing the fluid contained in the fluid holder with the dry reagent contained in the ampoule in accordance with an embodiment of the present invention.
Figure 23A:
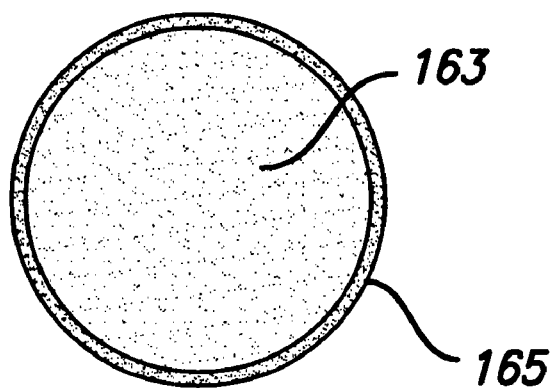
FIG. 23A is an axial perspective view of a breakable membrane.
Figure 23B:
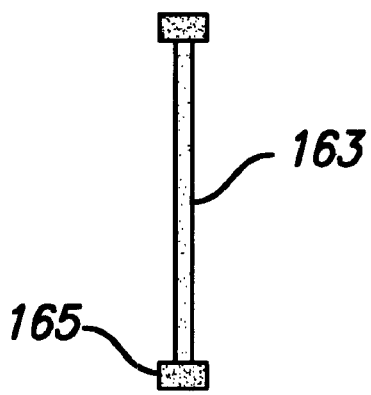
FIG. 23B is a side cross-sectional view of a breakable membrane in accordance with an embodiment of the present invention.

As depicted in FIGS. 12 and 23, in an embodiment of the instant invention, a fluid holder 112 may further include a breakable membrane 165 with a thin central portion 163 disposed at the base 167 of the attachment means 160. The breakable membrane may prevent the contents of the fluid holder 112 from coming into contact with the contents of the ampoule to which it is removably coupled. Since the dry reagent preferably contained within the ampoule may have a short shelf life once in contact with the fluid that is preferably contained within the fluid holder, it may be advantageous to prevent the two materials from contacting one another until soon before a mixture of the two materials is to be created and an injection administered therewith. Thus, the breakable membrane 165 is preferably circular to correspond to the inner circumference of the base 167 of the attachment means 160, and may be inserted into the attachment means cavity 169 prior to the fluid holder 112 being coupled to the ampoule 114 (as depicted in FIG. 13). The breakable membrane 165 may prevent fluid 158 contained in the fluid holder 112 from exiting through the orifice 162 into the ampoule 114 until a threshold level of force is applied by a user to the fluid holder plunger rod 164. When a sufficient level of force is applied, the internal pressure of the fluid 158 acting on the breakable membrane 165 preferably causes the breakable membrane 165 to rupture, and the contents of the fluid holder 112 are thus released through the orifice 162 into the ampoule. A mixture of the fluid 158 and the dry reagent 117 contained in the ampoule 114 may then be created within the ampoule 114 (as depicted in FIG. 14).

Breakable membrane 165 may be constructed of a material of sufficient mechanical properties and may be configured to be thin enough such that it readily ruptures at a predetermined level of force. Preferably, the requisite level of force is an amount high enough to avoid accidental rupture of the membrane, while low enough to allow a user to readily cause its breakage upon application of pressure on the fluid holder plunger rod 164. By way of example, the breakable membrane may be constructed of any plastic, rubber, metal or other suitable material. In a preferred embodiment, the membrane is constructed of polytetrafluoroethylene ("PTFE") or TEFLON® (available from E.I. duPont de Nemours & Co., Wilmington, Del.).

Figure 14:
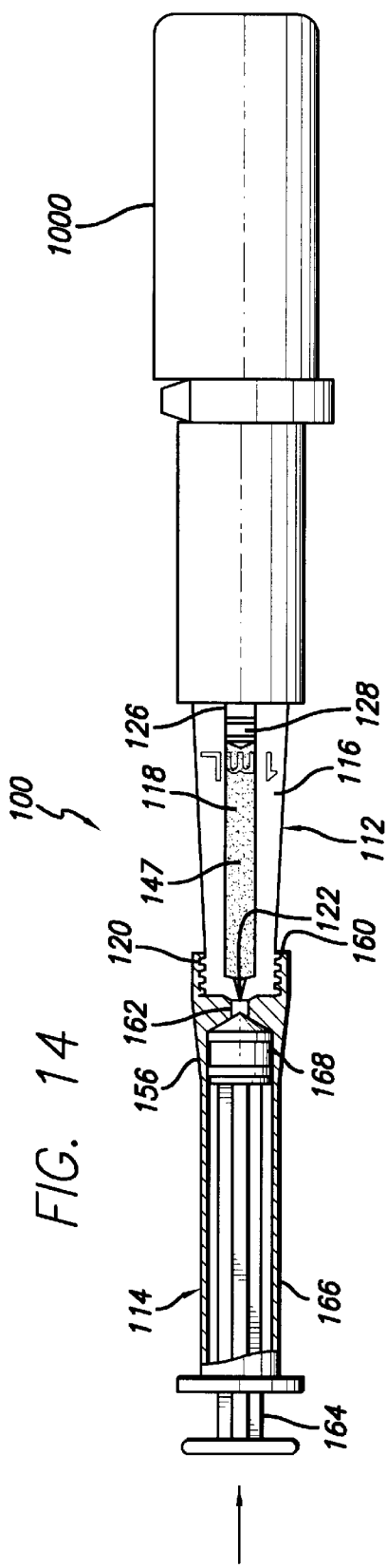
FIG. 14 is a cross-sectional view of the fluid holder, ampoule and needle-less injector depicted in FIG. 13 after mixing the fluid previously contained in the fluid holder with the dry reagent previously contained in the ampoule to create the mixture in the ampoule in accordance with an embodiment of the present invention.

FIGS. 13–17 further indicate the operation of an embodiment of the instant invention when the ampoule is coupled to a needle-less injector prior to creating a mixture of the fluid and dry reagent therein. Preferably, no ampoule plunger rod is included in this embodiment of the instant invention. FIG. 13 depicts the combination of an ampoule 112 coupled to a needle-less injector 1000 and a fluid holder 114. The fluid holder 114 contains a fluid 158 and the ampoule 112 contains a dry reagent 117. The fluid holder 114 and ampoule 112 are illustratively shown coupled together with screw threading. FIG. 14 depicts the same combination, the fluid holder plunger rod 164 having been depressed to load the fluid 158 into the interior cavity 118 of the ampoule 112, wherein it has mixed with the dry reagent 117 to form a mixture 147. The introduction of fluid 158 may result in the axial movement of the plunger 128 away from the orifice 122. FIG. 15 depicts the drawing of air or gas out from the interior cavity 118 of the ampoule 112 by pulling on the fluid holder plunger rod 164. FIG. 16 depicts the removal of the fluid holder 114 from the ampoule 112 and needle-less injector 1000. Finally, FIG. 17 depicts the removal of a safety clamp 1100 from the needle-less injector, such that an injection may be immediately administered.

Figures 21, 22:
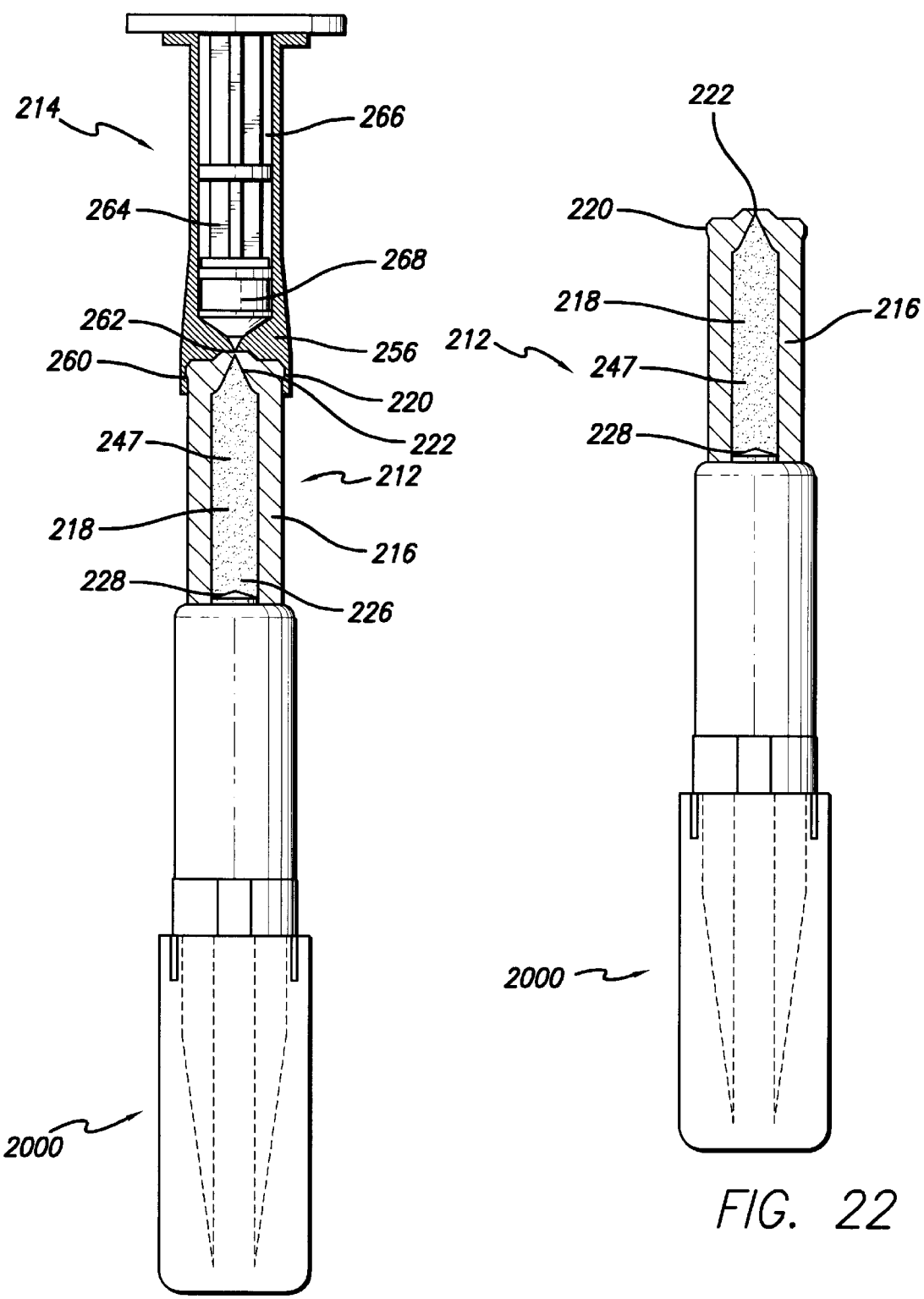
FIG. 21 is a cross-sectional view of the fluid holder and needle-less injector housing shown in FIG. 20, turned in a vertical orientation to optimize the removal of air or gas from the needle-less injector housing to the fluid holder in accordance with an embodiment of the present invention.
FIG. 22 is a cross-sectional view of the needle-less injector housing shown in FIG. 20, after the fluid holder is removed from the needle-less injector in accordance with an embodiment of the present invention.

FIGS. 18–23 indicate the operation of an embodiment of the instant invention when the needle-less injector includes a housing that acts as an ampoule. FIG. 18 depicts a needle-less injector 2000 that includes a housing 212. The housing 212 contains a dry reagent 217, and may include a cap 2200 which covers the dispensing end of the housing to prevent contamination of the dry reagent 217 contained therein. FIG. 19 depicts the combination of the needle-less injector 2000 with housing 212 and fluid holder 214 coupled together with a snap fitting attachment means. The fluid holder contains a fluid 258, and the dry reagent 217 remains in the interior cavity 218 of the housing 212. FIG. 20 depicts the same combination, the fluid holder plunger rod 264 having been depressed to load the fluid 258 into the interior cavity 218 of the housing 212, wherein it has mixed with the dry reagent 217 to form a mixture 247. The introduction of fluid 258 may result in the axial movement of the plunger 228 away from the orifice 222 FIG. 21 depicts the drawing of air or gas out from the interior cavity 218 of the housing 212 by first turning the combination in an approximately vertical orientation (i.e., the fluid holder 214 held above the needle-less injector 2000 and housing 212), and then pulling on the fluid holder plunger rod 264 (not shown). Finally, FIG. 22 depicts the needle-less injector 2000 with housing 212 filled with mixture 247, from which gas or air has been removed, such that an injection may be immediately administered.

While the description above refers to particular embodiments of the present invention, it will be understood that many modifications may be made without departing from the spirit thereof The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. In combination, an ampoule adapted for use with a needle-less injector and an apparatus for filling an ampoule of a needle-less injector suitable for injecting a mixture of a fluid and a dry reagent, the combination comprising:
the ampoule containing the dry reagent; and
a needle-free fluid holder containing the fluid,
wherein the needle-free fluid holder has a fluid plunger rod, said rod having a longitudinal axis,
the ampoule is matingly attached to the needle-free fluid holder to provide fluid communication between the ampoule and the needle-free fluid holder, and
the fluid plunger rod is configured to be slideably depressed, upon application of pressure along the longitudinal axis of the fluid plunger rod, to load the fluid into the ampoule of the needle-less injector thereby creating the mixture.

2. The combination of claim 1, wherein the ampoule is attached to the needle-free fluid holder by an attachment mechanism selected from the group consisting of mutual threads, snaps, and friction fits.

3. The combination of claims 1, further including a membrane disposed between the needle-free fluid holder and the ampoule, the membrane configured to rupture to provide fluid communication between the ampoule and the needle-free fluid holder upon the application of a predetermined level of pressure to the fluid plunger rod.

4. The combination of claim 3, wherein the membrane is constructed of polytetrafluoroethylene (PTFE).

5. The combination of claim 1, wherein the ampoule has an ampoule plunger rod, said rod being configured to be depressed to expel air or gas from the ampoule.

6. The combination of claim 1, wherein the dry reagent is a lyophilized pharmaceutical.

7. The combination of claims 1, wherein the fluid is loadable into the ampoule and mixed with the dry reagent just prior to injection of the mixture.

8. The combination of claim 1, wherein the ampoule is attachable to the needle-less injector after mixing the fluid with the dry reagent.

9. A method of filling an ampoule of a needle-less injector suitable for injecting a mixture of a fluid and a dry reagent, the method comprising:
matingly attaching a needle-free fluid holder containing the fluid directly to the ampoule to provide fluid communication between the ampoule and the needle-free fluid holder, the needle-free fluid holder including a fluid plunger rod having a longitudinal axis; and
slideably depressing the fluid plunger rod in a rotation-free manner by applying pressure along the longitudinal axis thereof to load the fluid into an ampoule containing the dry reagent thereby creating the mixture.

10. The method of claim 9, wherein after the fluid is loaded into the ampoule thereby creating the mixture, the method further comprises depressing an ampoule plunger rod to expel air or gas from the ampoule.

11. The method of claim 9, wherein matingly attaching the needle-free fluid holder includes using an attachment mechanism selected from the group consisting of mutual threads, snaps, and friction fits.

12. The method of claims 10, further comprising applying sufficient force to the fluid plunger rod to rupture a membrane disposed between the needle-free fluid holder and the ampoule, thereby providing fluid communication between the needle-free fluid holder and the ampoule.

13. The method of claim 10, wherein the ampoule is filled with fluid and the mixture created just prior to injection of the mixture.

14. The method of claim 10, further comprising attaching the ampoule to the needle-less injector after filling the ampoule with the fluid thereby creating the mixture.

15. The method of claims 12, wherein matingly attaching the needle-free fluid holder includes using an attachment mechanism selected from the group consisting of mutual threads, snaps, and friction fits.

16. An apparatus for mixing a fluid and a dry reagent and for filling an ampoule of a needle-less injector suitable for injecting a mixture of the fluid and the dry reagent, the apparatus comprising:
the ampoule containing the dry reagent; and
a needle-free fluid holder containing the fluid, and having a fluid plunger rod, said fluid plunger rod having a longitudinal axis, wherein the ampoule is matingly attached to the needle-free fluid holder to provide fluid communication between the ampoule and the needle-free fluid holder, and the fluid plunger rod is configured to be slideably depressed, upon application of pressure along the longitudinal axis of the fluid plunger rod, to load the fluid into the ampoule to mix with the dry reagent to produce the mixture in the ampoule of the needle-less injector.

17. An apparatus in accordance with claim 16, further including a membrane disposed between the needle-free fluid holder and the ampoule, the membrane configured to rupture to provide fluid communication between the ampoule and the needle-free fluid holder upon the application of a predetermined level of pressure to the fluid plunger rod.

18. The apparatus of claim 17, wherein the membrane is constructed of polytetrafluoroethylene (PTFE).

19. An apparatus in accordance with claim 16, wherein the ampoule further includes an ampoule plunger rod, and wherein after the dry reagent and the fluid are mixed in the ampoule, the ampoule plunger rod is depressable to expel air or gas from the ampoule.

20. An apparatus in accordance with claim 16, wherein the dry reagent and fluid are mixed just prior to injection of the mixture.

21. An apparatus in accordance with claim 16, wherein the ampoule is attached to the needle-less injector after producing the mixture in the ampoule.

22. An apparatus in accordance with claim 16, wherein the dry reagent is a lyophilized pharmaceutical.

23. An apparatus for mixing a fluid with a dry reagent in an ampoule of a needle-less injector, the apparatus comprising:

a needle-free fluid holder containing the fluid;

an attachment mechanism disposed on said needle-free fluid holder; and a fluid plunger rod disposed within the needle-free fluid holder and having a longitudinal axis, the fluid plunger rod configured to be slideably depressed, upon application of pressure along the longitudinal axis, wherein when the needle-free fluid holder is matingly attached directly to the ampoule of a needle-less injector by the attachment mechanism, fluid communication is provided between the needle-free fluid holder and the ampoule, and when the fluid plunger rod is depressed, the fluid and the dry reagent are mixed in the ampoule.

24. An apparatus in accordance with claim 23, further including a membrane, wherein when the needle-free fluid holder is attached to the ampdule, the membrane is disposed between the needle-free fluid. holder and the ampoule, the membrane being configured to rupture to provide fluid communication between the ampoule and the needle-free fluid holder upon the application of a predetermined level of pressure to the fluid plunger rod.

25. The combination of claim 24, wherein the membrane is constructed of polytetrafluoroethylene (PTFE).

26. An apparatus in accordance with claim 23, wherein the dry reagent and fluid are mixed just prior to injection of the mixture.

27. An apparatus in accordance with claim 23, wherein the dry reagent is a lyophilized pharmaceutical.

28. In combination, an ampoule adapted for use with a needle-less injector and an apparatus for filling an ampoule of a needle-less injector suitable for injecting a mixture of a fluid and a dry reagent, the combination comprising:

the ampoule containing a dry reagent; and a fluid holder containing a fluid, wherein the fluid holder has a fluid plunger rod, said rod having a longitudinal axis, the ampoule is matingly attached to the fluid holder to provide fluid communication between the ampoule and the fluid holder, and the fluid plunger rod is configured to be slideably depressed, upon application of pressure along the longitudinal axis of the fluid plunger rod, to load the fluid into the ampoule of the needle-less injector thereby creating the mixture of the dry reagent and the fluid;

wherein the ampoule has an ampoule plunger rod, said rod being configured to be depressed to expel air or gas from the ampoule.

29. A method of filling an ampoule of a needle-less injector suitable for injecting a mixture of a fluid and a dry reagent, the method comprising the steps of:

providing a fluid holder containing a fluid;

providing the fluid holder with a fluid plunger rod having a longitudinal axis;

adapting the fluid holder to be matingly attached directly to an ampoule to provide fluid communication between the ampoule and the fluid holder;

slideably depressing the fluid plunger rod in a rotation-free manner by applying pressure along the longitudinal axis thereof to load the fluid into an ampoule containing a dry reagent thereby creating a mixture of the dry reagent and the fluid;

providing an ampoule containing a dry reagent;

providing an ampoule plunger rod for the ampoule; and after the fluid is loaded into the ampoule thereby creating the mixture of the dry reagent and the fluid, depressing the ampoule plunger rod to expel air or gas from the ampoule.

30. The method of claim 29, further comprising the steps of:

providing a membrane configured between the fluid holder and the ampoule, the membrane preventing fluid communication between the ampoule and the fluid holder; and applying sufficient force to the fluid holder plunger rod to rupture the membrane and thereby provide fluid communication between the fluid holder and the ampoule.

31. The method of claim 29, wherein the ampoule is filled with fluid and the mixture of the fluid and the dry reagent created just prior to injection of the mixture due to a short shelf life of the mixture.

32. The method of claim 29, further comprising the step of attaching the ampoule to the needle-less injector after filling the ampoule with the fluid thereby creating the mixture.

33. The method of claim 30, wherein the step of adapting includes using an attachment mechanism selected from the group consisting of mutual threads, snaps, and friction fits.

* * * * *